United States Patent [19]

Quang et al.

[11] Patent Number: 4,769,012
[45] Date of Patent: Sep. 6, 1988

[54] GRAVITY INFUSION AND TRANSFUSION FLOW REGULATING DEVICE

[75] Inventors: Minh B. Quang, Stockelsdorf; Gert Urbschat, Neustadt, both of Fed. Rep. of Germany

[73] Assignee: Codan Medizinische Geräte GmbH & Co. KG, Fed. Rep. of Germany

[21] Appl. No.: 54,623

[22] Filed: May 27, 1987

Related U.S. Application Data

[63] Continuation of Ser. No. 792,964, Oct. 30, 1985, abandoned.

[51] Int. Cl.⁴ ..................... A61M 5/005; F16K 15/14
[52] U.S. Cl. ..................... 604/247; 604/32; 604/248; 604/256; 137/504; 137/852
[58] Field of Search ............ 604/31, 32, 246–248, 604/256, 122, 252, 141; 251/208, 341, 345; 137/504, 852, 859

[56] References Cited

U.S. PATENT DOCUMENTS

| | | | |
|---|---|---|---|
| 3,092,142 | 6/1963 | Willson | 251/208 |
| 3,190,496 | 6/1965 | Weiland, Jr. et al. | 137/859 |
| 3,599,131 | 8/1971 | Flanagan et al. | 251/208 |
| 3,630,484 | 12/1971 | Taylor | 251/208 |
| 3,812,882 | 5/1974 | Taylor | 251/208 |
| 3,838,794 | 10/1974 | Cogley et al. | 604/141 |
| 3,877,428 | 4/1975 | Seagle et al. | 604/248 |
| 4,136,693 | 5/1977 | Duke | 604/248 |
| 4,198,971 | 4/1980 | Noiles | 604/126 |
| 4,252,116 | 2/1981 | Genese et al. | 137/859 |
| 4,298,358 | 11/1981 | Ruschke | 604/126 |
| 4,332,247 | 6/1982 | Mittleman et al. | 604/122 |
| 4,343,305 | 8/1982 | Bron | 604/248 |
| 4,428,397 | 1/1984 | Bron | 137/504 |
| 4,515,588 | 5/1985 | Amendolia | 604/247 |
| 4,712,583 | 12/1987 | Pelmulder et al. | 604/247 |
| 4,714,458 | 12/1987 | Hooven | 604/247 |

FOREIGN PATENT DOCUMENTS 2167161  5/1986  United Kingdom ............ 604/4

Primary Examiner—Stephen C. Pellegrino
Assistant Examiner—Ralph Lewis
Attorney, Agent, or Firm—McGlew and Tuttle

[57] ABSTRACT

A flow regulating device for gravity infusion and transfusion of fluids comprises upper and lower housing parts which include inflow and outflow channels respectively. A continuously adjustable valve is connected between the inflow and outflow channels. The outflow channel has an outlet opening which defines a valve seat and a membrane extends across the outlet opening and is movable toward and away from the outlet opening depending on pressure appearing on opposite sides of the membrane. In this way extraneous pressures, such as patient venous pressure, can be compensated for by the membrane to maintain a substantially constant flow of fluid once the valve is set.

8 Claims, 6 Drawing Sheets

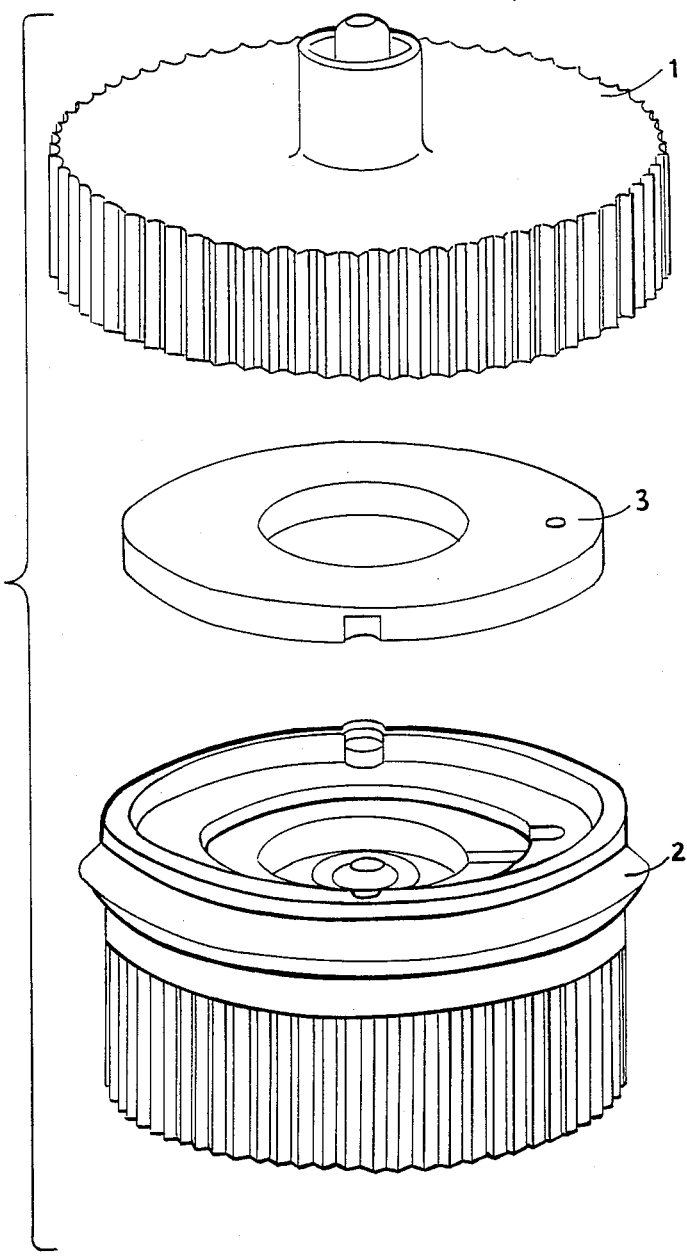

GRAVITY INFUSION AND TRANSFUSION FLOW REGULATING DEVICE

This is a continuation of application Ser. No. 792,964 filed Oct. 30, 1985, abandoned.

FIELD AND BACKGROUND OF THE INVENTION

The present invention relates in general to medical infusion devices and in particular to a new and useful device for regulating the flow in a gravity infusion or transfusion device which has a continuously adjustable valve positioned between an inflow channel and an outflow channel.

Such devices, which are currently used in hospitals, clinics and doctor's offices to regulate the flow of fluid to be administered, are frequently designed as roller clamps. Because of the creep characteristics of the tube used to carry the fluid, and the roller clamp, precise dose control cannot be achieved by one setting. As a rule, an exponential decline in drip speed is observable over the course of time. It is particularly difficult to maintain a low drip rate within permissible tolerances for hours at a time.

Furthermore, drip speed is heavily influenced by the patient's venous pressure. When the patient sits up, for example, and his venous pressure thereupon rises, drip speed can decline by 50%.

SUMMARY OF THE INVENTION

The present invention seeks to solve the problem of creating an infusion and transfusion flow device whereby the patient's safety and the effectiveness of the medication to be administered by infusion or transfusion can be increased by permitting precise dose control through an even flow of the fluid. The inventive device operates independently of the fluid tube and also largely independently of the patient's venous pressure, so that the drip rate can be kept constant once it is set.

Accordingly an object of the present invention is to provide a device for regulating flow in gravity infusion and transfusion, with a continuously adjustable valve positioned between an inflow channel and an outflow channel for fluid, comprising closeable throttle means provided in the fluid flow stream at a point upstream of the valve, the throttle means having a membrane and an outlet opening to the outflow channel, an opposite side of the membrane from the outflow channel cooperating with the inflow channel for regulating flow between the inflow and the outflow channels according to pressures exerted on opposite sides of the membrane.

Pursuant to the invention, not only is a valve permitting continuous regulation of flow provided, but a second, parallel mechanism affecting flow, and consisting of the membrane, is included. This membrane is affected by the pressure in the inflow channel as well as the pressure in the outflow channel and thus shifts under the influence of these pressures. Together with the outlet opening of the outflow channel, the membrane constitutes a throttle point which regulates flow in light of the patient's venous pressure in that the pressure upstream of the outlet opening of the outflow channel increases because of the increased flow resistance in the bloodstream and hence the membrane is raised more forcibly from the outlet opening. The increase in the patient's venous pressure can thus be compensated for by a reduction in the throttle effect of the membrane before the outlet opening, and hence a steady flow speed can be achieved. When venous pressure drops, of course, the opposite adjustment takes place.

The drip rate of the fluid is kept constant by a combination of steady fine-dose control and the adjustment of flow to changes in the patient's venous pressure.

A further object of the invention is to provide such a flow regulating device for gravity infusion and/or transfusion devices which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

The invention will now be explained in greater detail in terms of possible embodiments thereof, and with reference to the drawings wherein:

FIG. 2 is a perspective exploded view of the device in FIG. 1;

FIG. 3b is a bottom plan view taken in the direction of the arrow in FIG. 3a;

FIG. 4b is a sectional view taken on line 4b—4b of FIG. 4a;

FIG. 5b is a view taken along line 5b—5b of FIG. 5a;

FIG. 6b is a view taken along line 6b—6b of FIG. 6a;

FIG. 7a is the same view as in FIG. 4a, but with the valve open somewhat wider than in FIG. 6a;

FIG. 7b is a view taken along line 7b—7b of FIG. 7a; and

DESCRIPTION OF THE PREFERRED EMBODIMENTS

Figure 1:
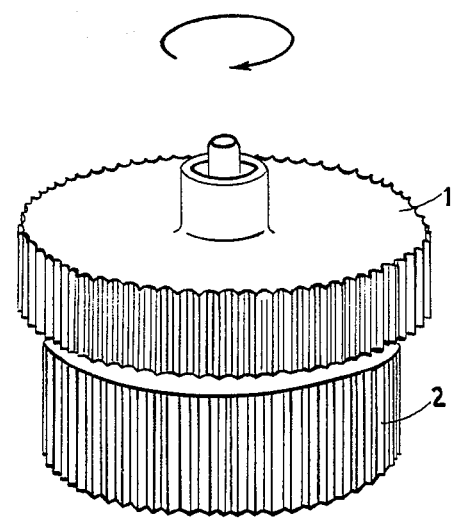
FIG. 1 is a perspective view of device pursuant to the invention.

The device shown in the drawings consists of three major elements, an upper part 1, a lower part 2 and a disc 3. Since the upper part 1 can turn with respect to parts 2 and 3, these parts are designed to be essentially cylindrical.

Figure 3A:
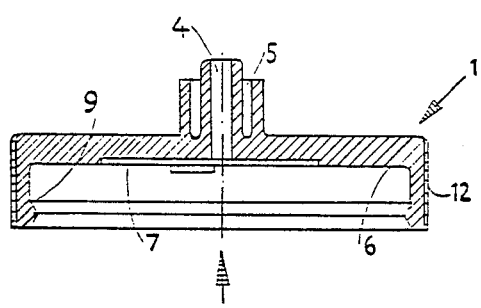
FIG. 3a is a sectional view of an upper part for the inventive flow regulating device.
Figure 3B:
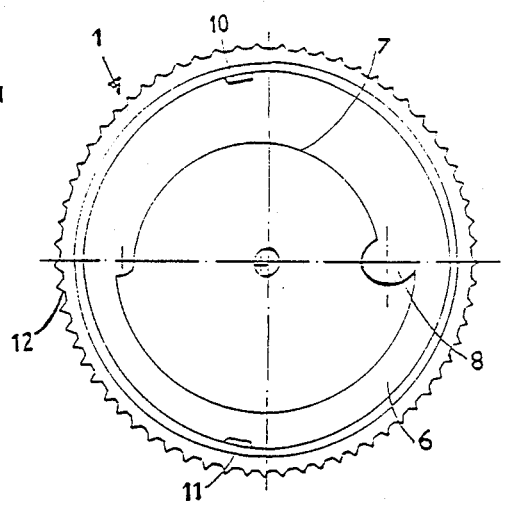

Upper part 1 has an inflow channel 4 and a cone 5 to connect with an upper fluid tube (not shown). At the base 6 of part 1 is an eccentric step plate or recess 7 with a lug 8 as shown in FIGS. 3a and 3b. The rotation angle between parts 1 and 2 can be limited by two stops 10 and 11. An undercut 9 in part 1 forms part of a snap connection with the lower part 2. The knurling 12 makes it easier to grasp and turn the upper part by hand.

Figure 3C:
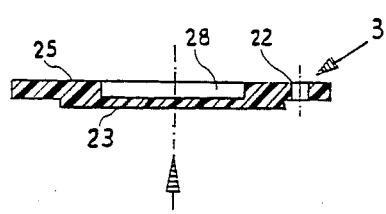
FIG. 3c is a sectional view of the membrane.
Figure 3E:
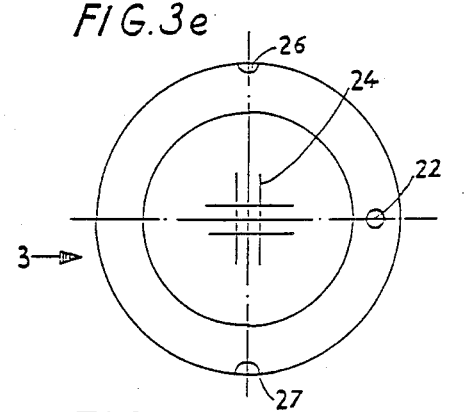
FIG. 3e is a bottom plan view taken in the direction of the arrow in FIG. 3c.
Figure 3D:
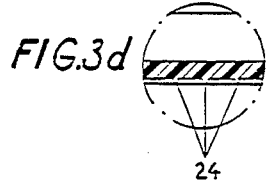
FIG. 3d is an enlarged detail of FIG. 3c.
Figure 3F:
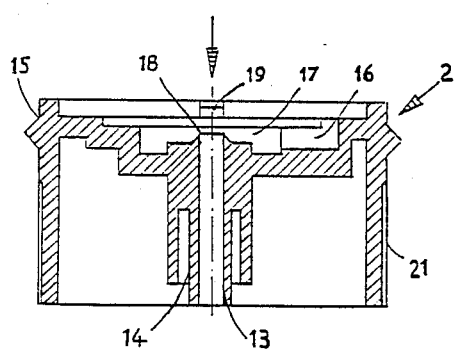
FIG. 3f is a sectional view of the lower part of the flow regulating device.
Figure 3G:
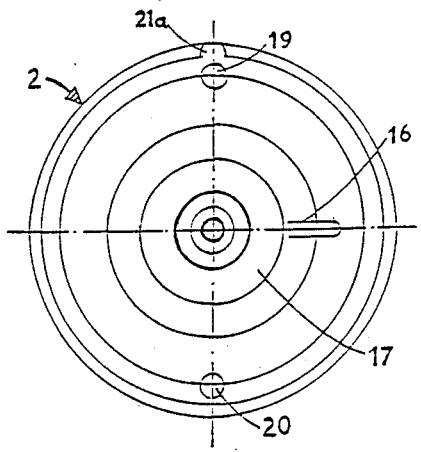
FIG. 3g is a top plan view taken in the direction of the arrow of FIG. 3f.

The lower part 2 as shown in FIGS. 3f and 3g, is equipped with an outflow channel 13 and a cone 14 to connect with a lower fluid tube (not shown). A channel 16 directs flow to a chamber 17. Two cylindrical stops 19 and 20 serve to hold the disc 3 in place. Counterpart or projection 21a for stops 10 and 11 prevent the upper part 1 from turning too far. Projection 21a extends upwardly from an annular nose 15 on part 2. Nose 15 serves to create a snap connection with undercut 9 of the upper part 1. The knurling 21 makes it easier to hold the lower part firmly in the hand.

The disc 3 as shown in FIGS. 3c and 3e, which fits snugly into the lower part 2 and has a valve opening 22 that serves as a connecting channel between the upper and lower parts, is equipped with a chamber 28, which is open to the inflow channel 4. The disc is of an elastomer material and has a thin, flexible membrane 23 in its mid-section relative to its main portion such that the membrane containing mid-section forms a corresponding expansion recess facing the upper part 1.

Since the disc is slightly thicker than the seat provided for it in the lower part 2, it forms a tight fit with its surface 25 against the base 6 of the upper part 1 when the device is assembled.

The upper part 1 is mounted on the lower part 2 by means of the snap connection (undercut 9 and nose 15) and rests upon it with turning capability. Concomitant turning of the disc 3 is prevented by negative ears or recesses 26 and 27 on the disc and the corresponding positive counterparts or projections 19 and 20 on the lower part on which recesses 26 and 27 engage. The valve opening 22 in the disc is thus also fixed into position over the channel 16 in the lower part. The membrane 23 of the disc divides the space between upper part and lower part into two chambers 17 and 28 which inherently serve as intermediate expansion chambers, as compared to the corresponding flow cross sections of inflow channel 4, valve opening 22, valve channel 16, outflow channel 13, and outlet opening 18 at the top of outlet channel 13.

Figure 4A:
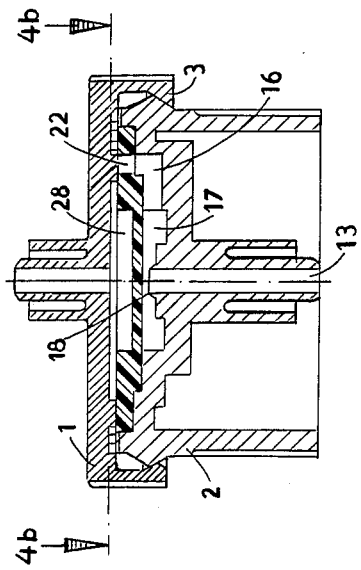
FIG. 4a is a sectional view of the device with the valve closed.
Figure 4B:
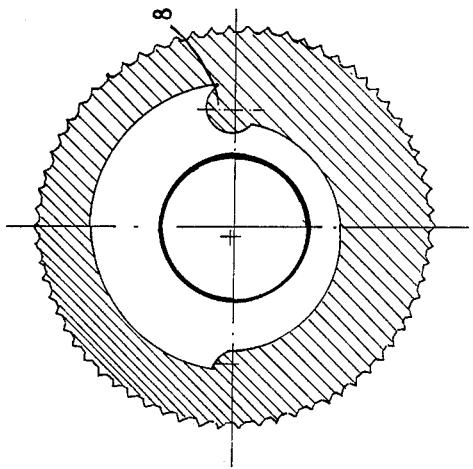

In FIGS. 4a and 4b the device is shown in longitudinal section and cross-section in a closed position. In this position, the lug 8 of the upper part completely covers the valve opening 22 and thus blocks all flow.

Figure 5A:
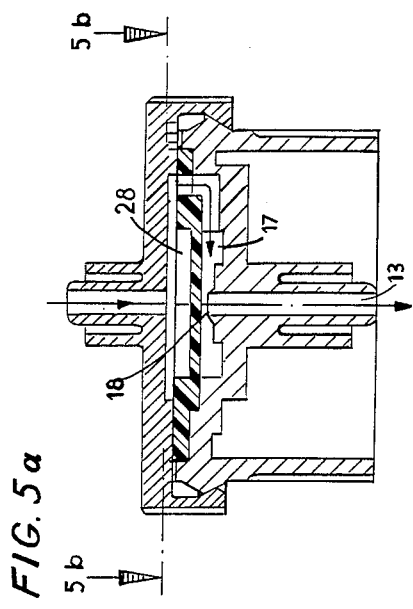
FIG. 5a is the same view as in FIG. 4a, but with the valve fully open.
Figure 5B:
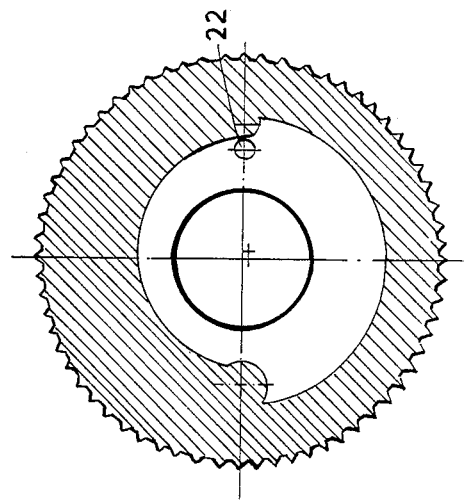
Figure 7A:
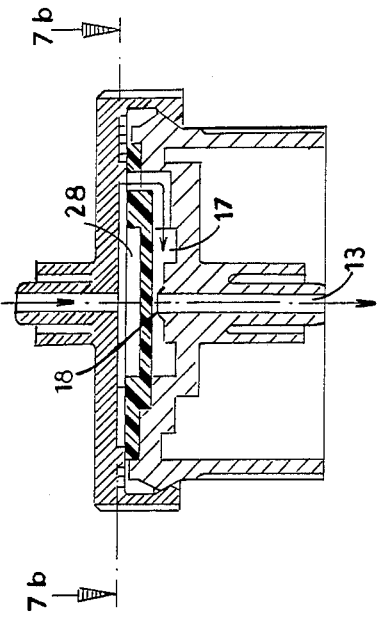
Figure 7B:
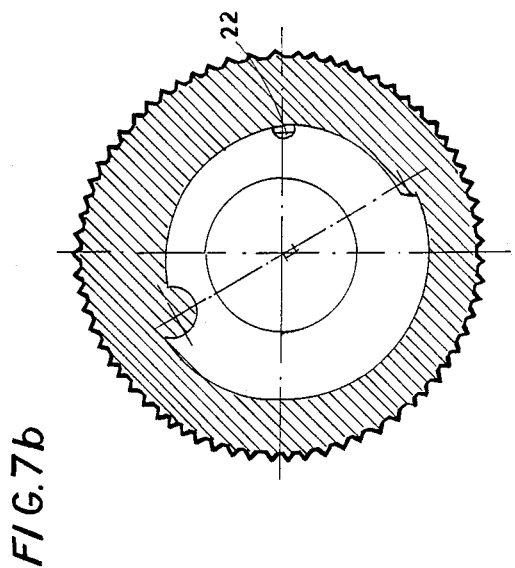
Figure 6A:
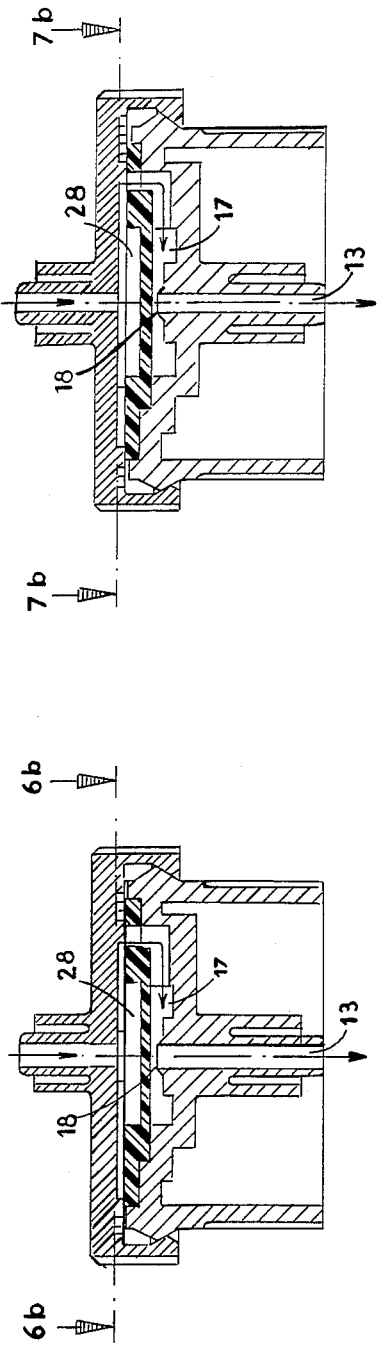
FIG. 6a is the same view as in FIG. 4a but with the valve almost closed.
Figure 6B:
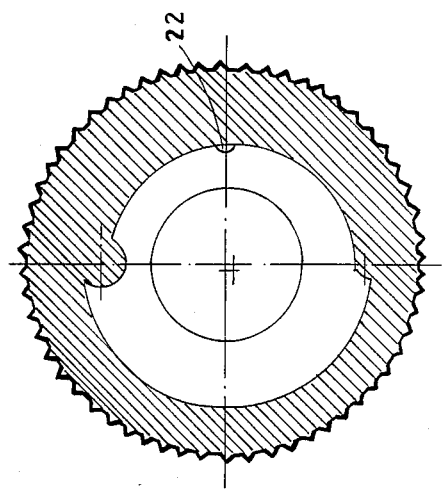

Dose control over the flow of the fluid is possible because, as the upper part turns with respect to the lower part, the eccentric step plate 7 on the base of the upper part covers the valve opening 22 of the disc to a greater or lesser degree and thus adjusts the flow of fluid. This is clear from examination of FIGS. 4a through 7b. The flow of fluid is represented by arrows. FIGS. 5a and 5b show the valve fully open, FIGS. 6a and 6b show it slightly open and FIGS. 7a and 7b show it almost fully open.

The fluid runs through the valve opening 22 and the channel 16 and then enters chamber 17 under the membrane 23. As long as chamber 17 is not yet filled with fluid, the membrane lies firmly pressed against the surface of the outlet opening 18 at the top of outlet channel 13 that constitutes a valve seat because of the stronger hydrostatic pressure in the chamber 28 above the membrane. The outlet opening 18 is here designed to be sharply-angled or conical. Furthermore, ribs 24 (FIGS. 3d and 3e) are provided on the underside of the membrane to prevent the membrane from adhering too tightly in the area of the outlet opening 18. The pressure in chamber 17 gradually builds up to that when the pressure is sufficient the membrane is raised and the outlet opening 18 is freed. A specific flow resistance is set in this manner for a specific height difference between the fluid container and the device constituting the flow regulator, and the fluid can flow continuously through the outflow channel.

The regulation of flow when the patient's intravascular pressure (venous pressure) increases is accomplished in the following manner: The pressure just upstream of the outlet opening 18 of the outflow channel 13 (under the membrane) increases due to the increased flow resistance in the bloodstream, and the membrane 23 is raised more forcibly. The increase in the patient's venous pressure can thus be compensated for by a decrease in the throttling effect of the membrane in front of the outlet opening, thus achieving a constant flow speed.

By examining the principle by which the flow regulator operates, it is clear that a constant flow speed is achieved by maintaining the total flow resistance constant. When a given drop rate is set, a fixed and specific flow resistance comes about as a result of the throttling effect of the valve opening 22 by the action of the eccentric step plate 7. The effect of the membrane 23 upstream of the outlet opening 18 of the outflow channel constitutes the variable element of flow resistance. This variable flow resistance serves to compensate for the increased venous pressure of the patient and thus makes it possible to control flow.

One prerequisite for the regulation of flow is that the membrane must be able to be lifted by the increase in the intravascular pressure. Furthermore, the difference in the hydrostatic pressure above and below the membrane also contributes to the force raising the membrane. In one embodiment, the ratio of the diameter of the outflow channel 13 to the diameter of the chamber 17 lies between 0.1 and 0.2. Apart from this ratio, the optimum thickness of the membrane 23 also depends on the material of the disc.

The flow regulator is attached at a specific interval below the drip chamber. Since the force to lift the membrane depends on the pressure differential above and below the membrane, the drip rate should not be affected by the position in which the patient is lying.

The flow regulator is independent of the tube, i.e. the drip rate is not affected by the creep characteristics of the tube as with a roller clamp.

With this turnable flow regulator, it is possible both to achieve precise dose control and regulate flow.

Flow rates of less than three drops per minute and over 500 ml/hour can be achieved.

By extending the lower part 2 with a sufficiently long handle, the flow regulator may be operated with one hand, with the upper part 1 being turned with the thumb and index finger.

Figure 8:
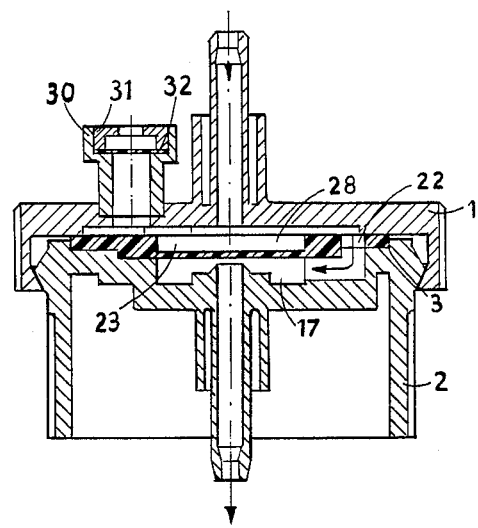
FIG. 8 is a sectional view of another embodiment of the invention, equipped with a deaerator.

FIG. 8 shows another embodiment equipped with a deaerator. When infusion bottles are changed quickly, using the same infusion set, experience has shown that a certain quantity of air can get into the tube system. To prevent the danger of an air embolism, this air is usually removed by disconnecting the infusion equipment from the patient. To perform this task, the nursing staff must be properly trained. It also requires time on the part of the nursing staff. Furthermore, it can happen that a small volume of air in the tube goes unnoticed by the nursing staff and gets into the bloodstream.

In order to be sure of removing these intrusions of air, a deaeration opening, with flow resistance no greater than the throttle resistance of the opening of valve 22, leads into chamber 28 above the membranes 23 into which the inflow channel empties. In FIG. 8 this deaeration opening is shown with a filter housing 30, a filter holder 31 and an air filter 32. The air filter is water-repellant, so that it will not become wetted by the fluid.

The air is collected in the upper chamber 28. This does not alter the flow of the fluid substantially, so that the required tolerances are met. When a somewhat larger quantity of air gets into the flow regulator, or when the air collected on a number of occasions builds up to such a large volume that the throttle resistance at valve 22 is overcome, this volume of air is very quickly (in one motion) driven out through the deaeration opening.

While specific embodiments of the invention have been shown and described in detail to illustrate the application of the principles of the invention, it will be understood that the invention may be embodied otherwise without departing from such principles.

What is claimed is:

1. Flow regulating device for the gravity infusion and transfusion of fluids, comprising
    an inlet part having an inflow channel of selective flow cross section for receiving fluid and an inflow expansion portion of increased flow cross section relative to the inflow channel for receiving fluid from the inflow channel,
    an outlet part having an outflow channel provided with an upstream outlet opening of selective flow cross section and an outflow expansion portion of increased flow cross section relative to the outlet opening for receiving fluid from the inflow expansion portion and passing fluid from the outflow expansion portion via the outlet opening to the outflow channel,
    continuously adjustable valve means connected between the inflow expansion portion and the outflow expansion portion for regulating the amount of fluid to be passed from the inflow channel to the outflow opening of the outflow channel,
    the valve means including a valve opening and a valve member movable relative to each other in a range for regulating a cross sectional area of the valve opening, from a completely closed position in which the valve member completely covers over the valve opening, through a continuous series of increasingly open intermediate positions in which the valve member increasingly uncovers such cross sectional area of the valve opening, to a completely open position in which the valve member completely uncovers the valve opening,
    a disc member disposed between the inlet and outlet parts and having an inlet side facing the inlet part and an outlet side facing the outlet part, the disc member being provided with a main portion of selective thickness disposed between the inlet and outlet parts, and a mid-section in the form of a flexible membrane of reduced thickness relative to the main portion and forming an expansion recess portion in the inlet side of the disc member,
    the membrane extending over the outlet opening of the outflow channel and being movable toward and away from the outlet opening depending on pressures exerted on opposite sides of the membrane,
    the inlet side of the disc member being shaped for defining in its mid-section expansion recess portion with the inflow expansion portion of the inlet part an inlet expansion chamber communicating with the inflow channel, and the outlet side of the disc member being shaped for defining with the outflow expansion portion of the outlet part an outlet expansion chamber surrounding the outflow channel,
    the outlet part including a valve channel communicating the valve opening with the outlet expansion chamber, and
    the outlet expansion chamber communicating with the outlet opening when the membrane is spaced away from the outlet opening, said outflow channel being provided with an acutely angled edge forming a valve seat around the outlet opening and for the membrane, and the membrane including a plurality of ribs facing the outlet opening for engaging the angled edge.

2. Device of claim 1 wherein the valve means comprises a lower portion having the valve opening, and an upper portion rotatably mounted to the lower portion and having an eccentric plate form valve member movable over the valve opening for regulating a cross sectional area of the valve opening with rotation of the upper portion with respect to the lower portion.

3. Device of claim 2 wherein the inlet part comprises an upper part which includes the upper portion, the disc member includes the lower portion and the valve opening, the inflow expansion portion includes the plate form valve member in the form of an eccentric step plate recess facing the expansion recess portion of the disc member for regulating the cross sectional area of the valve opening and defining with the disc member expansion recess portion the inflow expansion chamber, the outlet part comprises a lower part which includes the valve channel, the valve channel communicates directly with the valve opening of the disc member, and the upper part is rotatably mounted to the lower part.

4. Device of claim 3 wherein the disc member is tightly engaged between the upper and lower parts and fixed with respect to the lower part for rotation of the upper part with respect thereto.

5. Device of claim 4 wherein the lower part includes at least one projection, and the disc member correspondingly includes at least one projection accommodating recess engaged with said at least one projection for maintaining the disc member at a fixed rotational position with respect to the lower part when the upper part rotates.

6. Device of claim 1 wherein the inlet part includes a deaeration opening communication with the inflow expansion chamber and having a flow resistance no greater than a throttle resistance of the valve opening.

7. Device of claim 6 wherein an air filter is disposed across the deaeration opening.

8. Device of claim 7 wherein the air filter is made of water-repellant material.

* * * * *